United States Patent
Choi et al.

(10) Patent No.: US 10,525,064 B2
(45) Date of Patent: Jan. 7, 2020

(54) ANTICANCER ADJUVANT CONTAINING PANAXADIOL GINSENOCIDE COMPOUND

(71) Applicant: INTELLIGENT SYNTHETIC BIOLOGY CENTER, Daejeon (KR)

(72) Inventors: Chul Hee Choi, Daejeon (KR); Eun Soo Kim, Seoul (KR); Kyung Sun Choi, Daejeon (KR); Seung Wook Ryu, Daejeon (KR); Jin Gang Hou, Daejeon (KR)

(73) Assignee: Intelligent Synthetic Biology Center, Daejeon (KR)

( * ) Notice: Subject to any disclaimer, the term of this patent is extended or adjusted under 35 U.S.C. 154(b) by 0 days.

(21) Appl. No.: 15/575,787

(22) PCT Filed: Jul. 2, 2015

(86) PCT No.: PCT/KR2015/006832
§ 371 (c)(1),
(2) Date: Nov. 20, 2017

(87) PCT Pub. No.: WO2016/190481
PCT Pub. Date: Dec. 1, 2016

(65) Prior Publication Data
US 2018/0140618 A1 May 24, 2018

(30) Foreign Application Priority Data
May 22, 2015 (KR) .................... 10-2015-0071477

(51) Int. Cl.
*A61K 31/575* (2006.01)
*A61K 31/704* (2006.01)
*A61P 35/00* (2006.01)
*A61K 31/7034* (2006.01)

(52) U.S. Cl.
CPC .......... *A61K 31/575* (2013.01); *A61K 31/704* (2013.01); *A61K 31/7034* (2013.01); *A61P 35/00* (2018.01)

(58) Field of Classification Search
None
See application file for complete search history.

(56) References Cited

U.S. PATENT DOCUMENTS

| 2003/0092638 A1 | 5/2003 | Huang et al. |
| 2012/0252768 A1 | 10/2012 | Iwasaki et al. |

FOREIGN PATENT DOCUMENTS

| CN | 104208073 A | * 12/2014 | ........... A61K 31/575 |
| JP | 2005504799 A | 2/2005 | |
| JP | 2011121926 A | 6/2011 | |
| JP | 2013529899 A | 7/2013 | |
| KR | 10-0553266 B1 | 2/2006 | |
| KR | 10-0633452 B1 | 10/2006 | |
| WO | 2004/056372 A1 | 7/2004 | |
| WO | 2011/142618 A2 | 11/2011 | |

OTHER PUBLICATIONS

Schniewind, B., Christgen, M., Kurdow, R., Haye, S., Kremer, B., Kalthoff, H., & Ungefroren, H. (2004). Resistance of pancreatic cancer to gemcitabine treatment is dependent on mitochondria-mediated apoptosis. International journal of cancer, 109(2), 182-188. (Year: 2004).*

Kluza, J., Marchetti, P., Gallego, M. A., Lancel, S., Fournier, C., Loyens, A., . . . & Bailly, C. (2004). Mitochondrial proliferation during apoptosis induced by anticancer agents: effects of doxorubicin and mitoxantrone on cancer and cardiac cells. Oncogene, 23(42), 7018. (Year: 2004).*

Kim et al, 'Protopanaxadiols, active ingredients of ginseng, enhance doxorubicin-induced cytotoxicity in human breast cancer cells via modulation of mitochondrial dynamics', Keystone symposia-Integrating metabolism and tumor biology, No. J1-2019 (2015).

Kang et al., "Ginseng intestinal metabolite-I (GIM-I) reduces doxorubicin toxicity in the mouse testis," Reproductive Toxicology, vol. 16, No. 3, pp. 291-298, (2002).

Park, Bonggoo et al, "Neutral sphingomyelinase 2 modulates cytotoxic effects of protopanaxadiol on different human cancer cells", BMC Complementary and Alternative Medicine, vol. 13, No. 194, pp. 1-11 (2013).

Li et al, "Ginsenoside metabolite compound K enhances the efficacy of cisplatin in lung cancer cells", Journal of thoracic disease, vol. 7, pp. 400-406 (2015).

First Office Action, Application No. 2017-560772, Japan Patent Office, dated Oct. 2, 2018.

* cited by examiner

*Primary Examiner* — Dale R Miller
(74) *Attorney, Agent, or Firm* — Gavrilovich, Dodd & Lindsey LLP

(57) ABSTRACT

The present invention relates to an anticancer adjuvant containing, as an active ingredient, protopanaxadiol (PPD) or a compound-K, which are types of panaxadiol ginsenoside compounds, and a pharmaceutical composition for treating cancer containing the anticancer adjuvant and an anticancer agent having mitochondria-mediated anticancer activity. The anticancer adjuvant containing the PPD or compound-K provided in the present invention as an active ingredient damages mitochondria in cancer cells, thereby aiding mitochondria-mediated anticancer activity, and thus can be widely used in safer treatment or alleviation of cancer using anticancer agents that exhibit mitochondria-mediated anticancer activity.

5 Claims, 12 Drawing Sheets
Specification includes a Sequence Listing.

SEQUENCE LISTING

```
<160> NUMBER OF SEQ ID NOS: 3

<210> SEQ ID NO 1
<211> LENGTH: 16
<212> TYPE: RNA
<213> ORGANISM: Artificial Sequence
<220> FEATURE:
<223> OTHER INFORMATION: control_siRNA

<400> SEQUENCE: 1
ccuacgccaa uuucgu                                                16
```

```
<210> SEQ ID NO 2
<211> LENGTH: 19
<212> TYPE: RNA
<213> ORGANISM: Artificial Sequence
<220> FEATURE:
<223> OTHER INFORMATION: Mfn1_siRNA

<400> SEQUENCE: 2
guguagauuc ugguaauga                                                 19

<210> SEQ ID NO 3
<211> LENGTH: 19
<212> TYPE: RNA
<213> ORGANISM: Artificial Sequence
<220> FEATURE:
<223> OTHER INFORMATION: Mfn2_siRNA

<400> SEQUENCE: 3
cgaugcaacu cuaucguca                                                 19
```

ANTICANCER ADJUVANT CONTAINING PANAXADIOL GINSENOCIDE COMPOUND

CROSS REFERENCE TO RELATED APPLICATIONS

This application is a U.S. National Stage Application filed under 35 U.S.C. § 371 and claims priority to International Application No. PCT/KR2015/006832, filed Jul. 2, 2015, which application claims priority to Korean Application No. 10-2015-0071477, filed May 22, 2015, the disclosures of which are incorporated herein by reference in their entirety.

TECHNICAL FIELD

The present invention relates to an anticancer adjuvant containing a panaxadiol-type ginsenoside compound. More specifically, the present invention relates to an anticancer adjuvant containing, as an active ingredient, protopanaxadiol (PPD) or compound-K (C-K), which are types of panaxadiol ginsenoside compounds; a pharmaceutical composition for treating cancer containing the anticancer adjuvant and an anticancer agent having mitochondria-mediated anticancer activity; and a food composition for ameliorating cancer diseases containing the anticancer adjuvant.

BACKGROUND

In recent years, the incidence of various kinds of adult diseases is rapidly increasing due to improvement of the living environment and changes in dietary life of modern people, and the incidence of chronic diseases such as cancer, atherosclerosis, stroke, diabetes, hypertension, etc., is significantly increasing due to excessive nutrition or unbalanced diet. In particular, cancer has been the leading cause of death from the past to the present. Major methods for treating cancer include drug therapy, surgery, and radiation therapy, etc., and various other methods are also being attempted. However, drug therapy inevitably causes side effects because it requires a high dose of an anticancer agent so as to provide an appropriate accumulation level of the anticancer agent in the lesions.

Meanwhile, as the inhibition of intercellular signaling through gap junction channels is recognized as an important biochemical marker of cancer development, those materials which inhibit the process are being recognized as materials having effects of preventing and inhibiting cancer. As an anticancer agent exhibiting an effect of inhibiting the intercellular signaling, doxorubicin (i.e., a type of quinone-based compounds) was developed. Doxorubicin is known to have anticancer activity against solid tumors such as breast cancer, ovarian cancer, liver cancer, etc., and thus it may also be used generally for the treatment of other cancers. It is known that when the dose of doxorubicin is decreased for safe treatment, the efficiency of anticancer treatment decreases significantly, whereas when the dose of doxorubicin is increased for effective cancer treatment, it causes a side effect of inhibiting intercellular signaling.

Various studies are underway to overcome side effects of anticancer agents. For example, Korean Patent No. 553266 discloses an anticancer composition, which contains quercetin, which has the effects of preventing the side effects of intercellular signaling caused by doxorubicin and increasing the inhibition of the activity of matrix metalloproteinase, along with doxorubicin, and use thereof. Korean Patent No. 633452 discloses an anticancer agent containing a cocoa extract capable of recovering intercellular signaling through gap junctions by compensating the side effect of doxorubicin (i.e., inhibition of intercellular signaling through gap junctions). However, the above techniques have a disadvantage in that they can only suppress the side effect of doxorubicin itself and cannot solve the side effect caused by the administration of an excessive dose of doxorubicin. Since most side effects of anticancer agents are known to be caused by the administration of an excessive dose of the agents for improving their therapeutic effects, continuous efforts are being made to develop methods that can exhibit the same level of therapeutic effects even after treatment with a small amount of the anticancer agents.

Technical Problem

Under the circumstances, the present inventors have made efforts to develop a method for a safer anticancer treatment. As a result, they have discovered that protopanaxadiol (PPD) or compound-K (C-K) (i.e., types of protopanaxadiol (PPD) ginsenoside compounds) can aid the anticancer activity of doxorubicin, and thus when the doxorubicin is administered in combination with PPD or C-K, even a small amount of doxorubicin treatment can exhibit the same level of anticancer effect, thereby completing the present invention.

Technical Solution

An object of the present invention is to provide an anticancer adjuvant containing a protopanaxadiol (PPD)-type ginsenoside compound as an active ingredient.

Another object of the present invention is to provide a pharmaceutical composition for treating cancer diseases containing the anticancer adjuvant and an anticancer agent having mitochondria-mediated anticancer activity.

Still another object of the present invention is to provide a food composition for ameliorating cancer diseases containing the anticancer adjuvant.

Advantageous Effects of the Invention

The anticancer adjuvant containing, as an active ingredient, PPD or compound-K (C-K) provided in the present invention can damage mitochondria in cancer cells and aid mitochondria-mediated anticancer activity, and thus can be widely used for safer treatment or alleviation of cancer using anticancer agents that exhibit mitochondria-mediated anticancer activity.

BEST MODE

Figure 1:
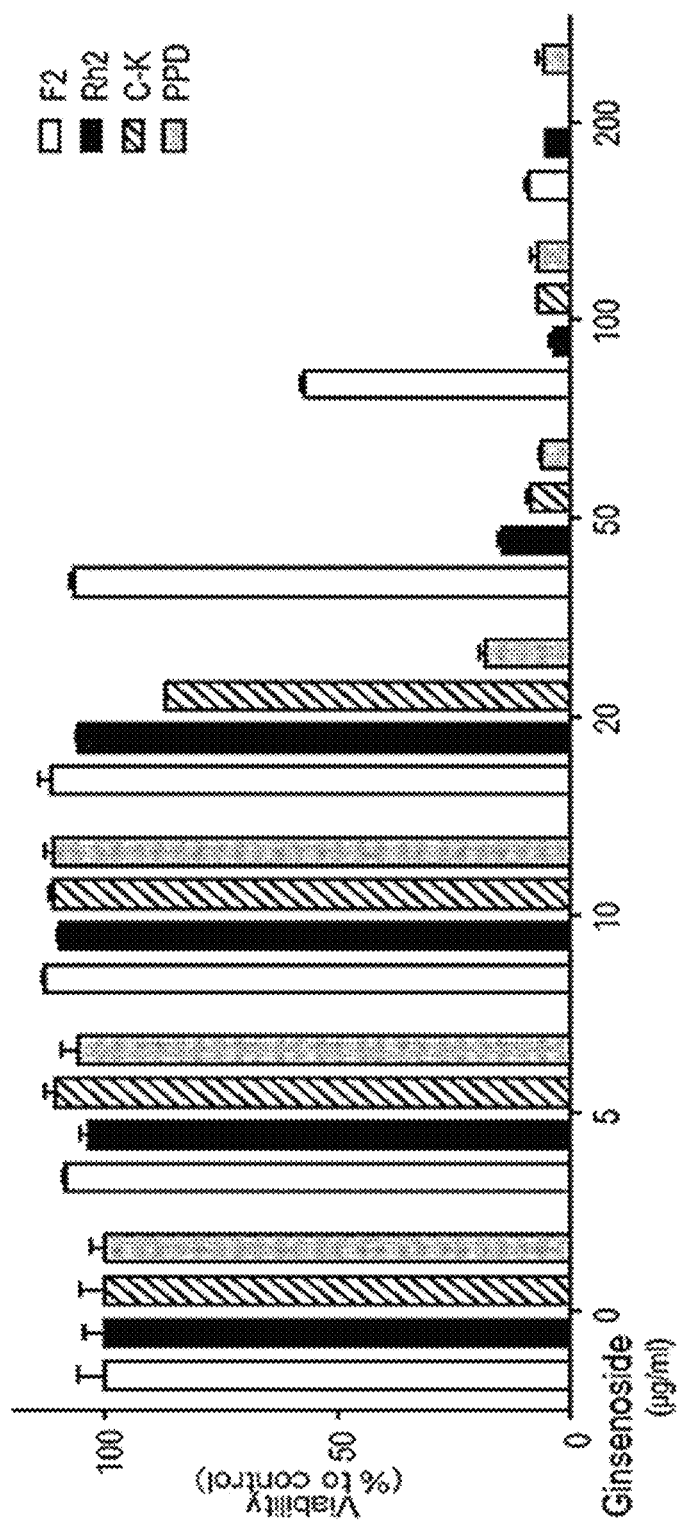
FIG. 1 shows a graph illustrating the comparison results with respect to the effects of PPD-type ginsenoside compound (F2, Rh2, C-K, or PPD) at various concentrations (0 μg/mL, 5 μg/mL, 10 μg/mL, 20 μg/mL, 50 μg/mL, 100 μg/mL, or 200 μg/mL) on the viability of MCF cells, which is a breast cancer cell line.

The present inventors have focused on protopanaxadiol (PPD)-type ginsenoside compounds while conducting various studies to develop a method for performing safer anticancer treatment. The PPD-type ginsenoside compounds are kinds of ginsenoside compounds contained in ginseng or red ginseng and may exhibit anticancer activity themselves, but they are known to exhibit various supplementary anticancer activities such as immunity enhancement and antioxidant activity in addition to direct anticancer activity, and thus the present inventors have attempted to confirm whether the PPD-type ginsenoside compounds can support the anticancer activity of other anticancer agents. As a result, it was confirmed that protopanaxadiol (PPD) or compound-K (C-K), which are kinds of PPD-type ginsenoside compounds, can induce mitochondrial fission of cancer cells and thereby damage the mitochondria. Although the effect of PPD or C-K inducing mitochondrial damage in cancer cells can aid the anticancer activity of those anticancer agents which exhibit mitochondria-mediated anticancer activity among various anticancer agents, the present inventors anticipated that the effect of inducing mitochondrial damage may not have an impact on the anticancer activity of other anticancer agents which exhibit anticancer activity by other mechanisms. As a result of their attempt to confirm the anticipation, it was confirmed that the induction of mitochondrial damage could improve the anticancer activity of doxorubicin, which exhibits mitochondria-mediated anticancer activity, but it did not affect the anticancer activity of tamoxifen, which acts as an antagonist to inhibit hormone-mediated cancer growth.

Therefore, it was confirmed that PPD or C-K can be used as an active ingredient of an anticancer adjuvant which can aid the anticancer activity of an anticancer agent exhibiting mitochondria-mediated anticancer activity, and such effect of PPD or C-K had not been known at all, having been first identified by the present inventors.

To achieve the above object, an aspect of the present invention provides an anticancer adjuvant containing PPD, C-K, or a combination thereof as an active ingredient.

As used herein, the term "protopanaxadiol (PPD)" refers to a compound which is represented by the formula of C3415203, has a molecular weight of 460 Da, and has the structure of Formula 1 shown below.

In the present invention, PPD may be used as an anticancer adjuvant to aid the mitochondria-mediated anticancer activity of an anticancer agent. The concentration of PPD to be used as anticancer adjuvant may not be particularly limited as long as PPD is able to aid the anticancer activity of a given anticancer agent while not exhibiting anticancer activity itself. In an exemplary embodiment, the concentration for treatment may be 10 µg/mL or less. In another exemplary embodiment, the concentration for treatment may be in a range of 0.1 µg/mL to 10 µg/mL. In still another exemplary embodiment, the concentration for treatment may be in a range of 5 µg/mL to 10 µg/mL.

[Formula 1]

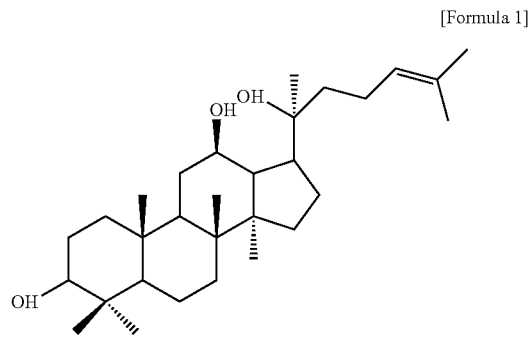

As used herein, the term "compound-K (C-K)" refers to a ginsenoside compound, which is not present in ginseng itself but converted from saponins (e.g., ginsenosides Rb1, Rb2, Rc, Rd, etc.), which are present in ginseng or red ginseng, into a form to be absorbed in the body by the action of intestinal microorganisms such as Bifidus bacteria or soil microorganisms. C-K is represented by the formula of $C_{36}H_{62}O_8$, has a molecular weight of 622 Da, and has the structure of Formula 2 shown below.

In the present invention, C-K may be used as an anticancer adjuvant to aid the mitochondria-mediated anticancer activity of an anticancer agent. The concentration of C-K to be used as anticancer adjuvant may not be particularly limited as long as C-K is able to aid the anticancer activity of a given anticancer agent while not exhibiting anticancer activity by itself. In an exemplary embodiment, the concentration for treatment may be 10 µg/mL or less. In another exemplary embodiment, the concentration for treatment may be in a range of 0.1 µg/mL to 10 µg/mL. In still another exemplary embodiment, the concentration for treatment may be in a range of 5 μg/mL to 10 μg/mL.

[Formula 2]

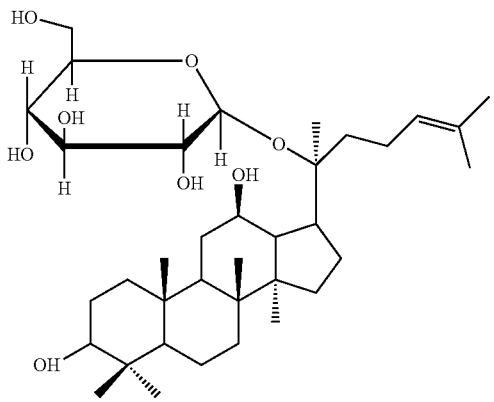

As used herein, the term "protopanaxadiol (PPD)-type ginsenoside compound" refers to a ginsenoside compound which has a structure similar to that of PPD.

In the present invention, the protopanaxadiol (PPD)-type ginsenoside compound compound may be interpreted as a compound having the role of aiding anticancer activity of an anticancer agent which exhibits mitochondria-mediated anticancer activity by damaging intracellular mitochondria. In an exemplary embodiment, the protopanaxadiol (PPD)-type ginsenoside compound may be PPD of Formula 1, C-K of Formula 2, etc. The protopanaxadiol (PPD)-type ginsenoside compound to be used may be those which are extracted from ginseng, red ginseng, etc., or one that is chemically synthesized.

As used herein, the term "anticancer adjuvant" refers to an agent capable of ameliorating, enhancing, or increasing anticancer activity of an anticancer agent.

In an exemplary embodiment, an agent which can ameliorate, enhance, or increase anticancer activity of an anticancer agent when used together with an anticancer agent may be used as an anticancer adjuvant.

In another exemplary embodiment, when an agent exhibiting anticancer activity in a concentration-dependent manner is used, at a level not exhibiting any anticancer activity itself, together with an anticancer agent the agent may be used as an anticancer adjuvant capable of ameliorating, enhancing, or increasing anticancer activity of the anticancer agent. In this case, the anticancer adjuvant may be used as an anticancer agent or anticancer adjuvant depending on the treatment concentration and may be used as an anticancer adjuvant in the range of treatment concentration that does not exhibit anticancer activity itself. For example, in the present invention, a PPD-type ginsenoside compound (PPD or C-K) was used as an anticancer adjuvant to aid the anticancer activity of an anticancer agent (doxorubicin) exhibiting mitochondria-mediated anticancer activity, and in particular, it was confirmed that the treatment concentrations of the PPD-type ginsenoside compound (PPD or C-K) that can be used as the anticancer adjuvant were 5 μg/mL and 10 μg/mL.

In the present invention, the anticancer adjuvant may be interpreted as an agent that performs the role of promoting the release of cytochrome-C from mitochondria by damaging intracellular mitochondria, and the anticancer adjuvant exhibits the effects of ameliorating, enhancing, or increasing anticancer activity of an anticancer agent exhibiting mitochondria-mediated anticancer activity. The anticancer agent exhibiting mitochondria-mediated anticancer activity that can enhance anticancer activity by the anticancer adjuvant is not particularly limited, but may be, for example, doxorubicin. In an exemplary embodiment, the cancer diseases that can be treated by the anticancer adjuvant may include solid cancers that can be treated by mitochondria-mediated anticancer activity, but are not particularly limited to. In another exemplary embodiment, the cancer diseases may be breast cancer, ovarian cancer, colon cancer, liver cancer, thyroid cancer, gallstone cancer, biliary tract cancer, pancreatic cancer, prostate cancer, esophageal cancer, cervical cancer, colon cancer, bladder cancer, central nervous system tumor, brain tumor, etc., and in still another exemplary embodiment, the cancer disease may be breast cancer.

Figure 4A:
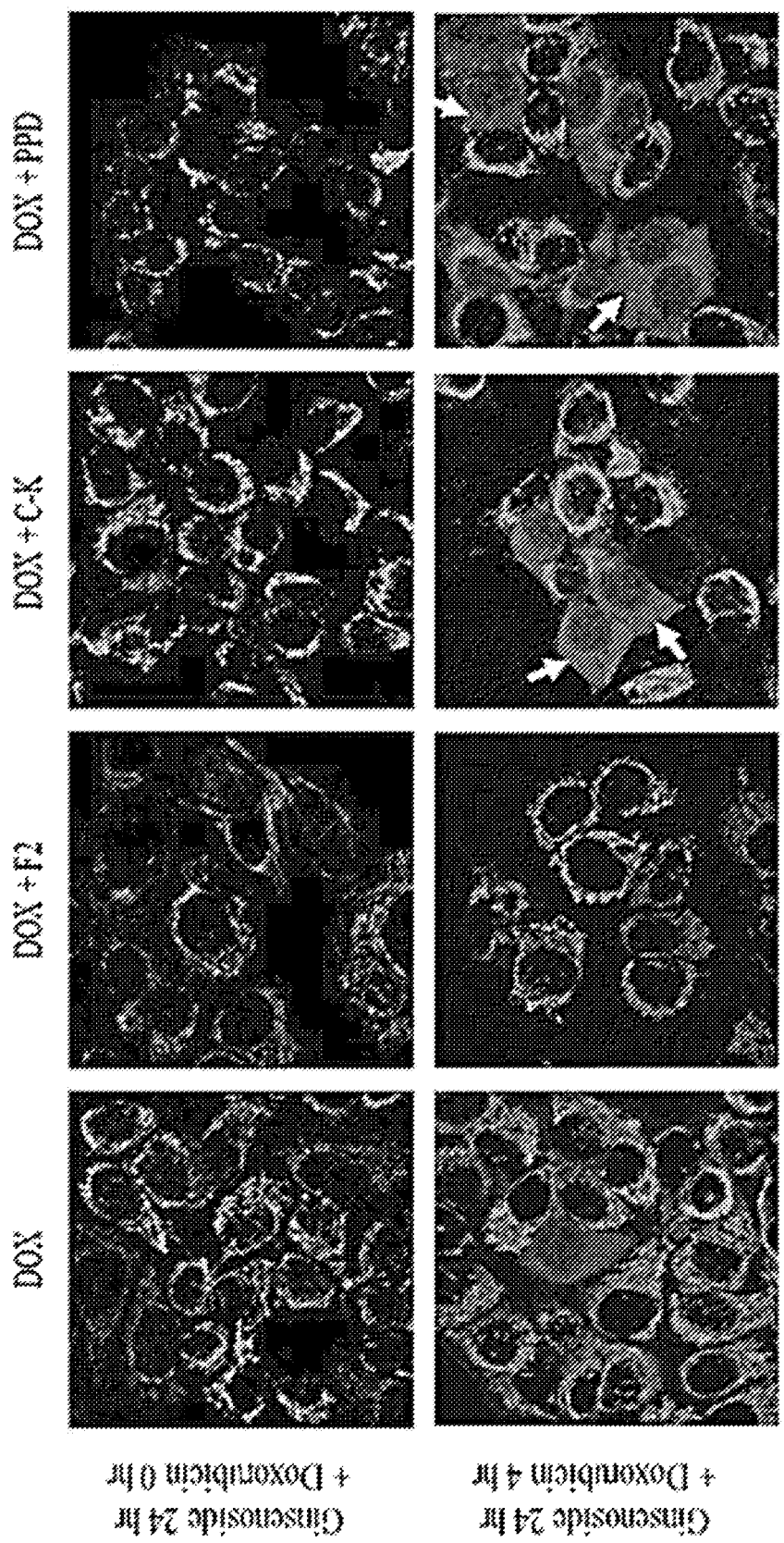
FIG. 4A shows immunofluorescent staining images illustrating the changes in the level of cytochrome-C released from mitochondria by simultaneous treatment with doxorubicin and C-K or PPD.
Figure 4B:
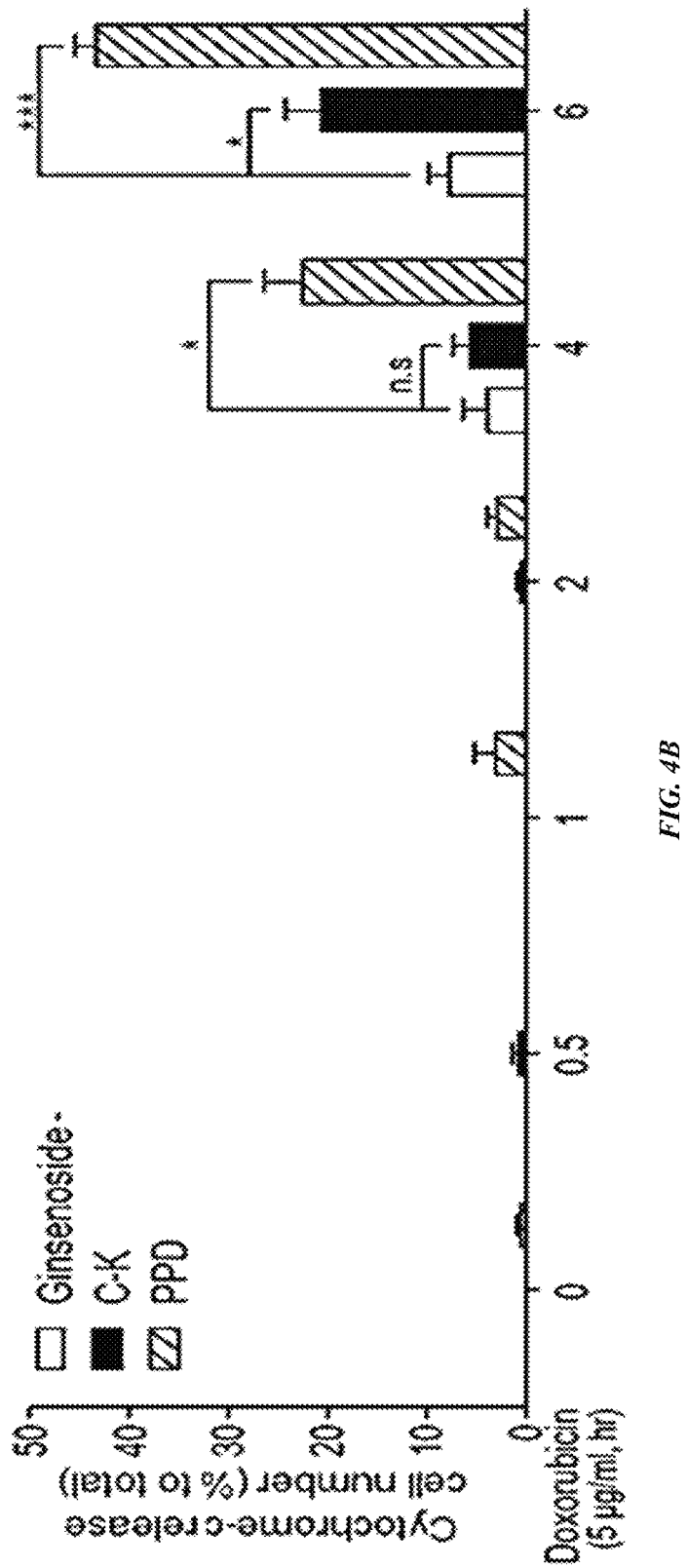
FIG. 4B shows a graph illustrating the number of cells in which cytochrome-C was released from mitochondria according to the time of simultaneous treatment with doxorubicin and C-K or PPD.
Figure 5A:
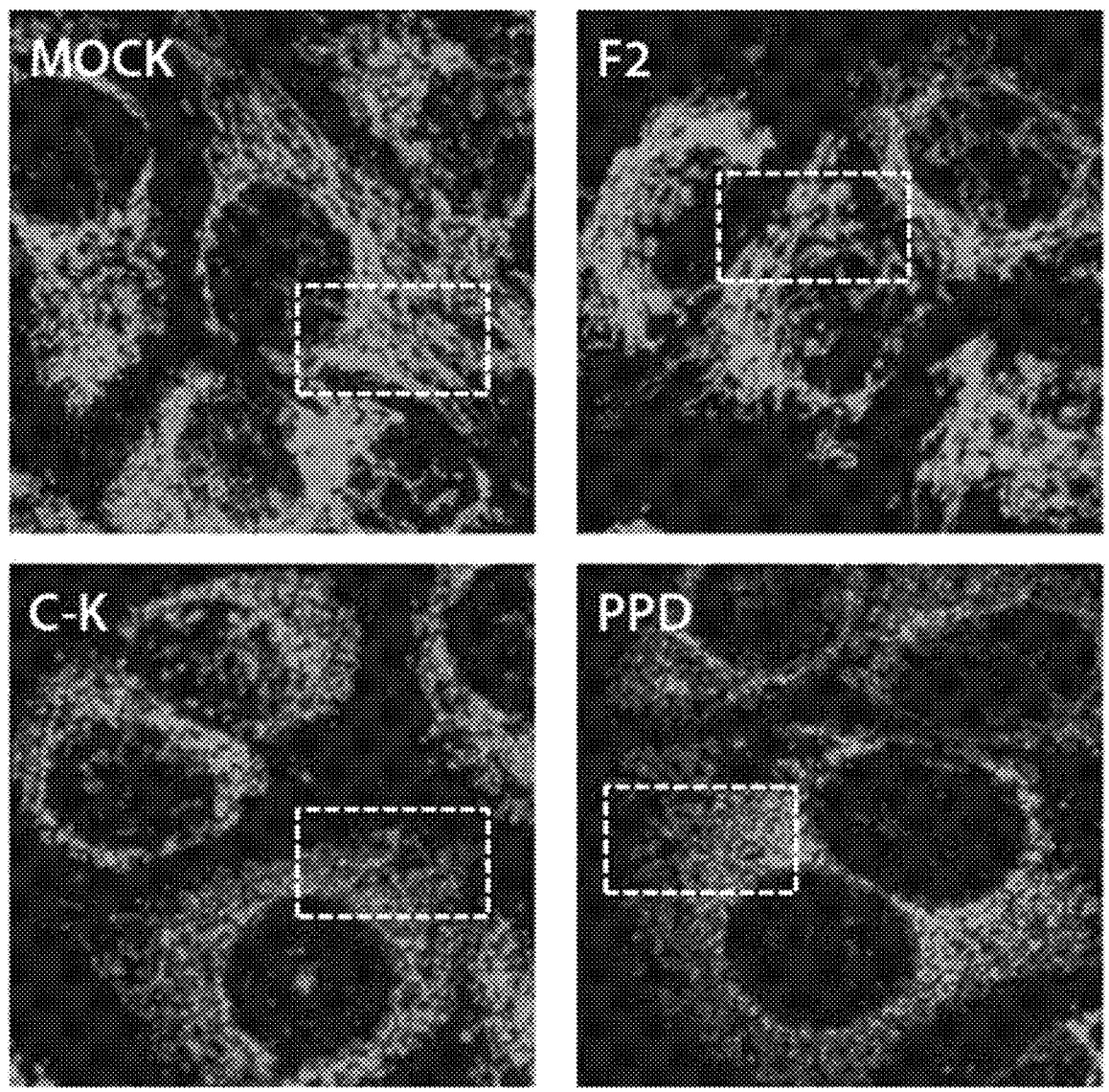
FIG. 5A shows immunofluorescent staining images of mitochondria contained in MCF-7 cells treated with C-K or PPD.
Figure 5B:
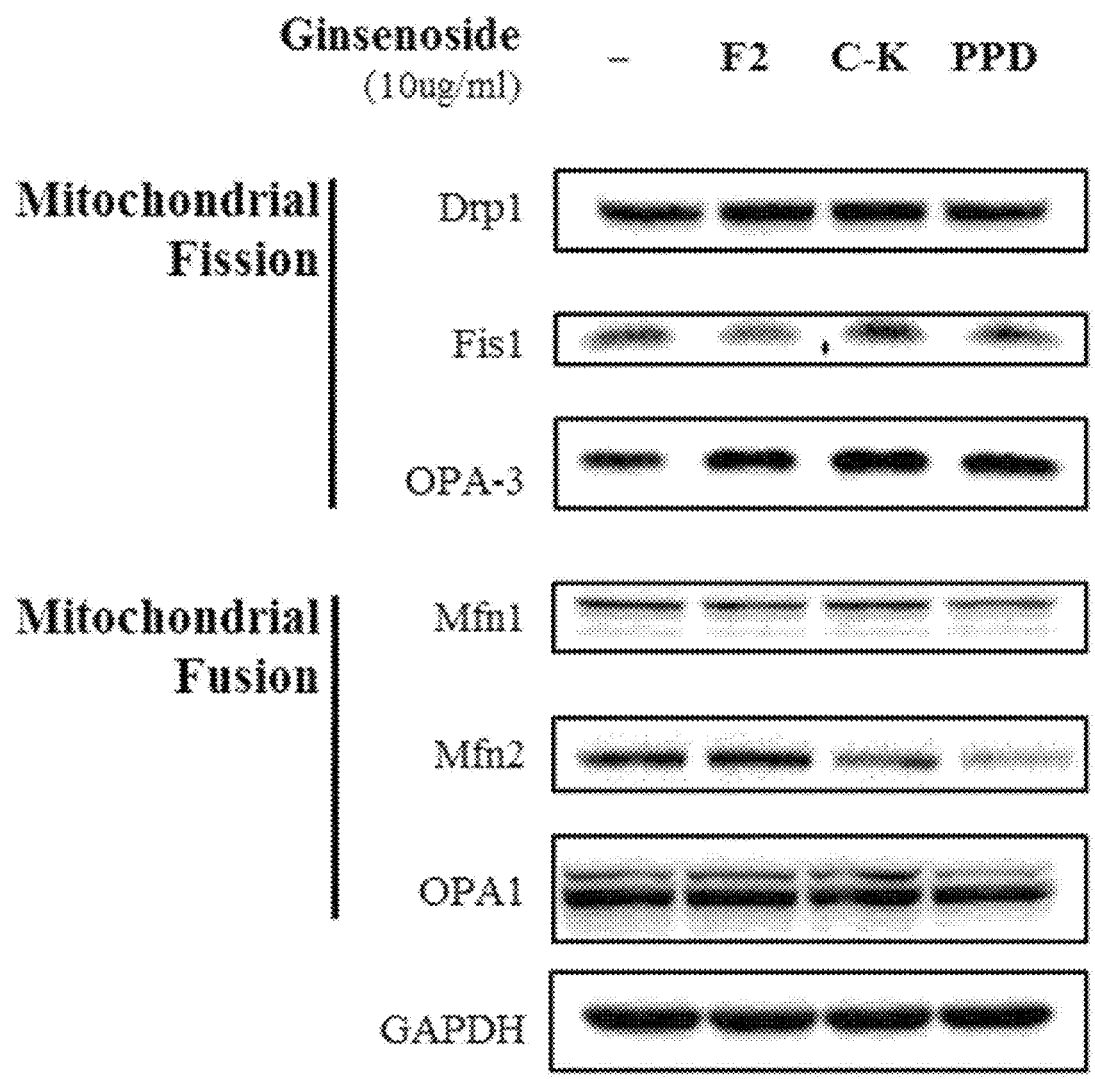
FIG. 5B shows an image of western blot analysis illustrating the expression levels of the proteins involved in mitochondrial fission (Drp1, Fis1, and OPA-3) and the proteins involved in mitochondrial fusion (Mfn1, Mfn2, and OPA1) expressed in MCF-7 cells treated with C-K or PPD.

According to an exemplary embodiment of the present invention, it was confirmed that the PPD-type ginsenoside compound can exhibit anticancer activity on breast cancer cells in a concentration-dependent manner (FIG. 1). However, when the PPD-type ginsenoside compound was treated at a dose not exhibiting anticancer activity, some of the PPD-type ginsenoside compounds (C-K or PPD) could aid the anticancer activity of doxorubicin (FIGS. 2A, 2B, 3A, and 3B). Since doxorubicin is known to exhibit mitochondria-mediated anticancer activity, the effects of the PPD-type ginsenoside compounds (C-K or PPD) on mitochondria were analyzed. As a result, it was confirmed that doxorubicin treatment can increase the level of cytochrome-C released from the mitochondria of breast cancer cells (FIGS. 4A and 4B) and damage the mitochondria of breast cancer cells by itself (FIGS. 5A and 5B). In this regard, when mitochondria were damaged by inducing mitochondrial fission and then treated with doxorubicin, an increase in anticancer activity of doxorubicin was observed (FIG. 6B).

Accordingly, it was confirmed that PPD or C-K belonging to the PPD-type ginsenoside compounds exhibit the effect of aiding anticancer activity of an anticancer agent exhibiting mitochondria-mediated anticancer activity.

The anticancer adjuvant of the present invention may be administered in combination with an anticancer agent or anticancer adjuvant exhibiting mitochondria-mediated anticancer activity so as to enhance the anticancer effect of the anticancer agent. In an exemplary embodiment, the anticancer adjuvant of the present invention may be co-administered with an anticancer agent such as doxorubicin, etoposide, daunorubicin, mitoxantrone, etc. When doxorubicin is administered in combination with the anticancer adjuvant of the present invention, even when doxorubicin is administered at a lower dose than the usual dose, it is possible to achieve an equivalent level of an anticancer therapeutic effect, and thus, a safer anticancer treatment can be performed.

The anticancer adjuvant may be administered via any of the common routes, as long as it is able to reach a target tissue. The anticancer adjuvant of the present invention may be administered according to the intended purposes via intraperitoneal, intravenous, intramuscular, subcutaneous, intradermal, oral, intranasal, intrapulmonary, or intrarectal administration, but the administration routes are not limited thereto. Additionally, the anticancer adjuvant may also be administered using any device capable of transferring the active material to the target cells.

Another aspect of the present invention provides a pharmaceutical composition for treating cancer diseases containing the anticancer adjuvant and an anticancer agent exhibiting mitochondria-mediated anticancer activity.

As described above, PPD or C-K, which are active ingredients of the anticancer adjuvant provided in the present invention, can perform the role of promoting the release of cytochrome-C from mitochondria by damaging the mitochondria in the cancer cells. Accordingly, when the anticancer adjuvant is used together with an anticancer agent exhibiting mitochondria-mediated anticancer activity, it can exhibit an increase in the effect of ameliorating, enhancing, or increasing anticancer activity of the anticancer agent, and thus the anticancer treatment can be more effectively performed. Additionally, since the anticancer adjuvant can ameliorate, enhance, or increase anticancer activity of the anticancer agent, the administration dose of the anticancer agent to be used for the purpose of exhibiting the equivalent anticancer activity can be reduced when the anticancer adjuvant is used together with an anticancer agent. Additionally, when the administration dose of the anticancer agent is reduced as such, the probability and level of occurrence of side effects that can be caused by administration of the anticancer agent can be reduced, thereby enabling a safer anticancer treatment.

Accordingly, as a more effective and safe preparation, the anticancer adjuvant may be formulated together with an anticancer agent exhibiting mitochondria-mediated anticancer activity.

Meanwhile, the cancer diseases that can be treated or ameliorated by the pharmaceutical composition are the same as described above.

The pharmaceutical composition of the present invention may be prepared in the form of a pharmaceutical composition for preventing or treating inflammatory diseases, further containing an appropriate carrier, excipient, or diluent which are conventionally used in the preparation of pharmaceutical compositions. Specifically, the pharmaceutical composition may be formulated into oral preparations such as powders, granules, tablets, capsules, suspensions, emulsions, syrups, aerosols, etc., preparations for external use, suppositories, and sterile injection solutions. In the present invention, examples of suitable carriers, excipients, and diluents to be contained in the pharmaceutical composition may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, etc. The formulations may be prepared using a commonly used diluent or excipient such as a filler, an extender, a binder, a humectant, a disintegrant, a surfactant, etc. Solid formulations for oral administration may include tablets, pills, powders, granules, capsules, etc., and these solid formulations may be prepared by adding at least one excipient (e.g., starch, calcium carbonate, sucrose or lactose, gelatin, etc.) to extract and fractions thereof. Additionally, a lubricant, such as magnesium stearate, talc, etc., may be used, in addition to the simple excipient. Liquid formulations for oral administration may include suspensions, liquid medicines for internal use, emulsions, syrups, etc., and various excipients such as humectants, sweeteners, fragrances, and preservatives, may be used, in addition to the simple diluents such as water and liquid paraffin. Formulations for parenteral administration may include sterile aqueous solutions, non-aqueous solvents, suspensions, emulsions, lyophilized formulations, suppositories. Examples of the non-aqueous solvents and suspensions may include vegetable oils such as propylene glycol, polyethylene glycol, and olive oil, an injectable ester such as ethyl oleate, etc. Examples of the bases for suppositories may include Witepsol, macrogol, Tween 61, cacao butter, laurinum, glycerogelatin, etc.

In an exemplary embodiment, PPD or C-K may be contained in the pharmaceutical composition of the present invention in an amount of 0.0001 wt % to 10 wt % based on the total weight of the final composition; and in another exemplary embodiment, PPD or C-K may be contained in an amount of 0.01 wt % to 3 wt %, and doxorubicin may be contained thereto in a known amount, but is not particularly limited thereto.

The pharmaceutical composition of the present invention may be administered in a pharmaceutically effective amount. As used herein, the term "pharmaceutically effective amount" refers to an amount sufficient for the treatment or prevention of diseases at a reasonable benefit/risk ratio applicable to a medical treatment or prevention, and the level of the effective dose may be determined based on the factors including severity of illness, drug activity, age, body weight, sex, drug sensitivity of a patient, administration time of the composition of the present invention used, administration route and dissolution rate, length of treatment, factors including drug(s) to be mixed or used simultaneously in combination with the composition of the present invention used, and other factors well-known in the medical field. The pharmaceutical composition of the present invention may be administered alone or in combination with other known therapeutic agent(s). It is important that the pharmaceutical composition of the present invention be administered in an amount to obtain the maximum effect with a minimum amount without adverse effects considering the factors described above.

The administration dose of the pharmaceutical composition of the present invention may be determined by one of ordinary skill in the art, considering the purpose of use, level of addition of a disease, a patient's age, sex, body weight, medical history, or the kind of a material used as an active ingredient. For example, the pharmaceutical composition of the present invention may be administered in an amount of about 0.1 ng/kg to about 100 mg/kg per adult, preferably about 1 ng/kg to about 100 mg/kg per adult. With regard to the administration frequency, the pharmaceutical composition of the present invention may be administered once daily or several times in divided doses, but is not particularly limited thereto. The administration dose should not limit the scope of the present invention in any manner.

Another aspect of the present invention provides a method for treating cancer diseases, including administering the pharmaceutical composition to a subject having a cancer disease in a pharmaceutically effective amount.

As used herein, the term "subject" may include, without limitation, mammals including mice, cattle, and humans, farmed fishes, etc., which have a risk of developing a cancer disease or have a cancer disease. The pharmaceutical composition of the present invention for treating cancer diseases may be administered via any of the common routes, as long as it is able to reach a target tissue. The pharmaceutical composition of the present invention may be administered according to the intended purposes via intraperitoneal, intravenous, intramuscular, subcutaneous, intradermal, oral, intranasal, intrapulmonary, or intrarectal administration, but the administration routes are not particularly limited thereto. Additionally, the anticancer adjuvant may also be administered by any device capable of transferring the active material to the target cells. However, since PPD or C-K may be denatured by gastric acid upon oral administration, the composition for oral administration should be coated or formulated for protection against degradation in the stomach. Additionally, the pharmaceutical composition may be administered using any apparatus capable of transporting the active ingredients contained therein into a target cell.

Still another aspect of the present invention provides a composition for ameliorating cancer diseases containing PPD or C-K.

PPD or C-K (i.e., active ingredients of the anticancer adjuvant) are derived from natural materials which have long been used as herbal drugs, and thus their safety is proven. Accordingly, PPD or C-K may be prepared in the form of foods that can promote the amelioration of cancer diseases while being consumed as regular dietary foods. That is, when the anticancer adjuvant is commonly taken as a food, it can amplify the anticancer effect of doxorubicin even when doxorubicin is administered at a low dose, and thus, the anticancer adjuvant may be contained in the food composition for ameliorating cancer diseases.

In particular, PPD or C-K may be contained in a food composition in an amount of 0.001 wt % to 10 wt %, and more preferably 0.1 wt % to 1 wt %, based on the total weight of the food composition, but is not particularly limited thereto. When the food is a drink, PPD or C-K may be contained in an amount of 1 g to 10 g, and preferably 2 g to 7 g, based on 100 mL of the drink. Additionally, the composition may further contain an additional ingredient which is commonly used in a food composition to enhance smell, taste, sight, etc. For example, the composition may include vitamins A, C, D, E, B1, B2, B6, and B12, niacin, biotin, folate, pantothenic acid, etc. The composition may also contain a mineral, such as zinc (Zn), iron (Fe), calcium (Ca), chromium (Cr), magnesium (Mg), manganese (Mn), and copper (Cu). The composition may also contain an amino acid, such as lysine, tryptophan, cysteine, and valine. The composition may further contain a food additive, such as antiseptics (e.g., potassium sorbate, sodium benzoate, salicylic acid, sodium dehydroacetate, etc.), disinfecting agents (e.g., bleaching powder and higher bleaching powder, sodium hypochlorite, etc.), antioxidants (e.g., butylhydroxyanisole (BHA), butylhydroxytoluene (BHT), etc.), colorants (e.g., tar dye, etc.), color-developing agents (e.g., sodium nitrite, etc.), bleaching agents (e.g., sodium sulfite), seasoning agents (e.g., MSG, sodium glutamate, etc.), sweeteners (e.g., dulcin, cyclamate, sodium saccharin, etc.), flavoring agents (vanillin, lactones, etc.), blowing agents (alum, potassium D-bitartrate, etc.), fortifying agents, emulsifying agents, thickening agents (adhesive pastes), coating agents, gum base agents, antifoaming agents, solvents, and improving agents. The additive may be selected and used in an appropriate amount according to food types.

Meanwhile, a health functional food for ameliorating cancer diseases may be prepared using a food composition for ameliorating cancer diseases containing PPD or C-K.

In a specific embodiment, processed foods for preventing or ameliorating cancer diseases may be prepared using the food composition. For example, a health functional food may be prepared in the form of confectioneries, beverages, alcohols, fermented foods, canned foods, milk-processed foods, meat-processed foods, or noodle-processed foods. In particular, the confectioneries may include biscuits, pies, cakes, breads, candies, jellies, gums, cereals (meal substitutes such as grain flakes, etc.), etc. Examples of the beverages may include drinking water, carbonated drinks, functional ion drinks, juices (e.g., apple, pear, grape, aloe, tangerine, peach, carrot, tomato juices, etc.), sweet rice drinks, etc. Examples of the alcohols may include refined rice wine, whiskey, soju, beer, liquor, fruit wine, etc. Examples of the fermented foods may include soy sauce, soybean paste, red pepper paste, etc. Examples of the canned foods may include canned marine products (e.g., canned products of tuna, mackerel, pacific saury, conch, etc.), canned meat products (canned products of beef, pork, chicken, turkey, etc.), canned agricultural products (canned products of corn, peach, pineapple, etc.), etc. Examples of the milk-processed products may include cheese, butter, yogurt, etc. Examples of the meat-processed foods may include pork cutlet, beef cutlet, chicken cutlet, sausage, sweet-and-sour pork, nuggets, Neobiani, etc. Noodles such as sealing-packed wet noodles may be included. Additionally, the food composition may be used in retort foods, soups, etc.

As used herein, the term "health functional food", which is the same term as food for special health use (FoSHU), refers to a food with high medicinal and medical effects to efficiently exhibit a bioregulatory function in addition to a function of nutrient supply. The health functional food may be prepared in various forms such as tablets, capsules, powders, granules, liquids, pills, etc. to obtain useful effects for ameliorating cancer diseases.

DETAILED DESCRIPTION OF THE INVENTION

Hereinafter, the present invention will be described in more detail with reference to the following Examples. However, these Examples are for illustrative purposes only and the invention is not intended to be limited by these Examples.

Example 1: Cytotoxicity of Protopanaxadiol (PPD)

An attempt was made to confirm whether protopanaxadiol (PPD)-type ginsenoside compounds exhibit cytotoxicity to cancer cells.

First, MCF-7 cells, a human breast cancer cell line, were inoculated into DMEM medium containing 10% FBS and 1% penicillin/streptomycin, cultured in conditions of 5% $CO_2$ and 37° C. When the cultured MCF-7 cells were saturated the cells were sub-cultured at intervals of 3 days to 5 days.

Then, the cultured MCF-7 cells were treated with various concentrations (0 μg/mL, 5 μg/mL, 10 μg/mL, 20 μg/mL, 50 μg/mL, 100 μg/mL, or 200 μg/mL) of PPD-type ginsenoside compounds (F2, Rh2, C-K, or PPD) for 24 hours, and the viability of these cells was measured by performing WST-1 assay on the MCF-7 cells (FIG. 1). In particular, WST-1 assay was performed by inoculating each of the MCF-7 cells in a medium containing 10% EZ-Cytox and reacting at 37° C. for 1.5 hours. The level of water-soluble formazan dye produced by the viable cells was measured by absorbance at 450 nm and the results were analyzed to calculate the cell viability of the cells.

FIG. 1 shows a graph illustrating the comparison results with respect to the effects of PPD-type ginsenoside compounds (F2, Rh2, C-K, or PPD) at various concentrations (0 μg/mL, 5 μg/mL, 10 μg/mL, 20 μg/mL, 50 μg/mL, 100 μg/mL, or 200 μg/mL) on the viability of MCF-7 cells, which is a breast cancer cell line. As shown in FIG. 1, it was confirmed that the PPD-type ginsenoside compounds have anticancer activity on breast cancer cells in a concentration-dependent manner. Although there were variations among compounds, anticancer activity generally began to appear when the MCF-7 cells were treated at a concentration of 20 μg/mL or more, and when treated at a concentration of 200 μg/mL or more, most of the breast cancer cells were shown to have been killed. In contrast, when the MCF-7 cells were treated at a concentration of 10 μg/mL or less, no anticancer activity was observed. In particular, among the PPD-type ginsenoside compounds, C-K or PPD showed relatively excellent anticancer activity. Accordingly, it was confirmed that the PPD-type ginsenoside compounds can exhibit anticancer activity against breast cancer cells in a concentration-dependent manner.

Example 2: Effect of PPD on Anticancer Activity of Doxorubicin

The effect of PPD-type ginsenoside compounds on doxorubicin, which is a kind of anticancer agent known to exhibit mitochondria-mediated anticancer activity, was studied.

Example 2-1: Effect of PPD on Sensitivity Cancer Cells to Doxorubicin

The effect PPD-type ginsenoside compounds on the sensitivity of cancer cells to an anticancer agent was examined using MCF-7 cells (i.e., a human breast cancer cell line), C-K or PPD (which were confirmed to exhibit excellent anticancer activity in Example 1), tamoxifen (which exhibits anticancer activity of inhibiting hormone-mediated cancer growth by acting as an antagonist of hormone receptors), and doxorubicin (which is a kind of anticancer agent known to exhibit mitochondria-mediated anticancer activity).

Specifically, each of the PPD-type ginsenoside compounds (F2, Rh2, C-K, or PPD) at a concentration of 10 μg/mL was added to MCF-7 cells, cultured for 12 hours, and treated with 20 μM tamoxifen or doxorubicin (5 μg/mL) and cultured for 24 hours. Upon completion of the cultivation, the viability of MCF-7 cells was compared by WST-1 assay (FIG. 2A).

Figure 2A:
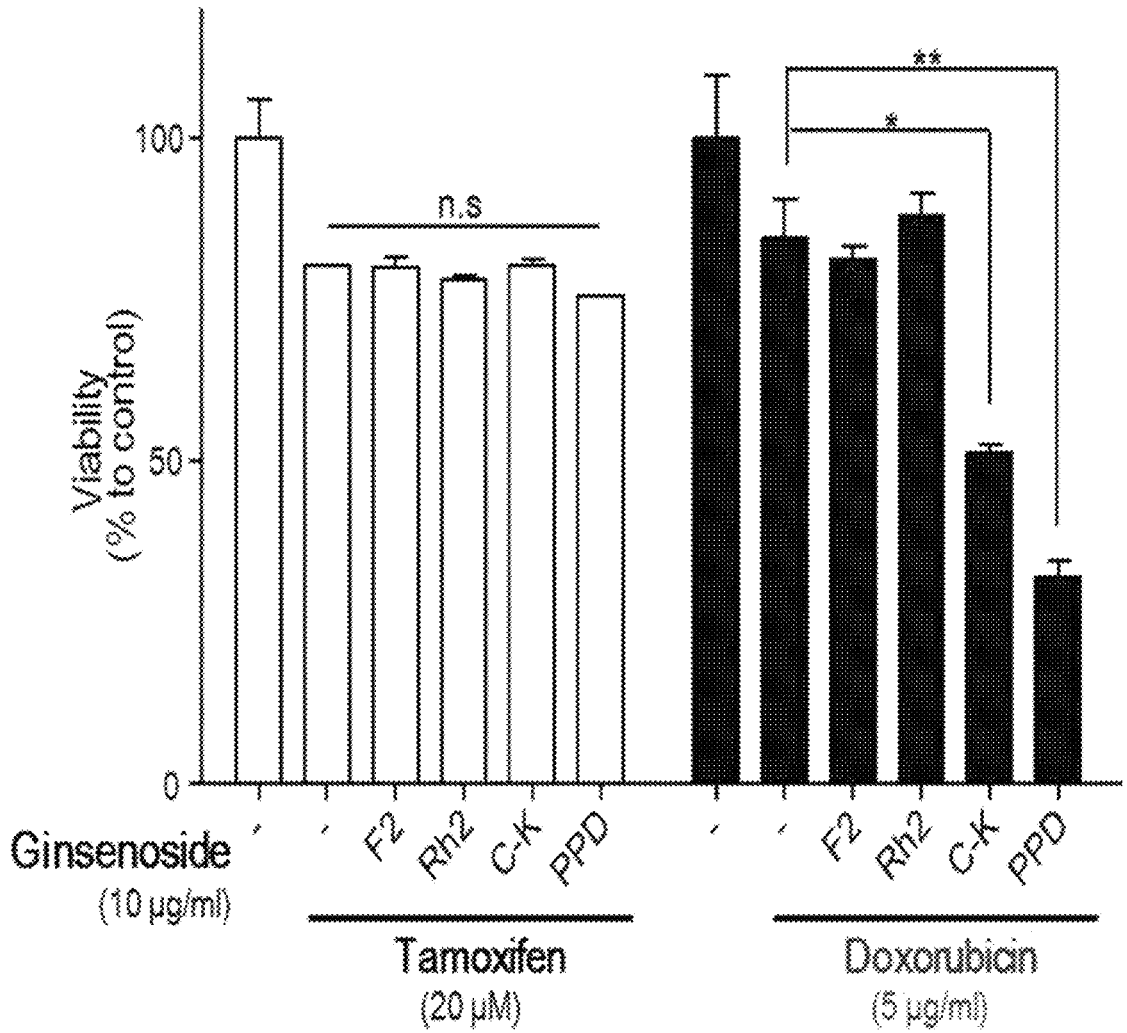
FIG. 2A shows a graph illustrating the comparison results with respect to the effects of PPD-type ginsenoside compound on their anticancer activity against cancer cells.

FIG. 2A shows a graph illustrating the comparison results with respect to the effects of PPD-type ginsenoside compounds on the anticancer activity against cancer cells. As shown in FIG. 2A, it was confirmed that when breast cancer cells were treated with a PPD-type ginsenoside compounds at a concentration not exhibiting anticancer activity at all followed by treatment with an anticancer agent, C-K or PPD among the PPD-type ginsenoside compounds could enhance the anticancer activity of doxorubicin. In contrast, when breast cancer cells were treated with tamoxifen, none of the PPD-type ginsenoside compounds were shown to enhance the anticancer activity of tamoxifen.

Figure 2B:
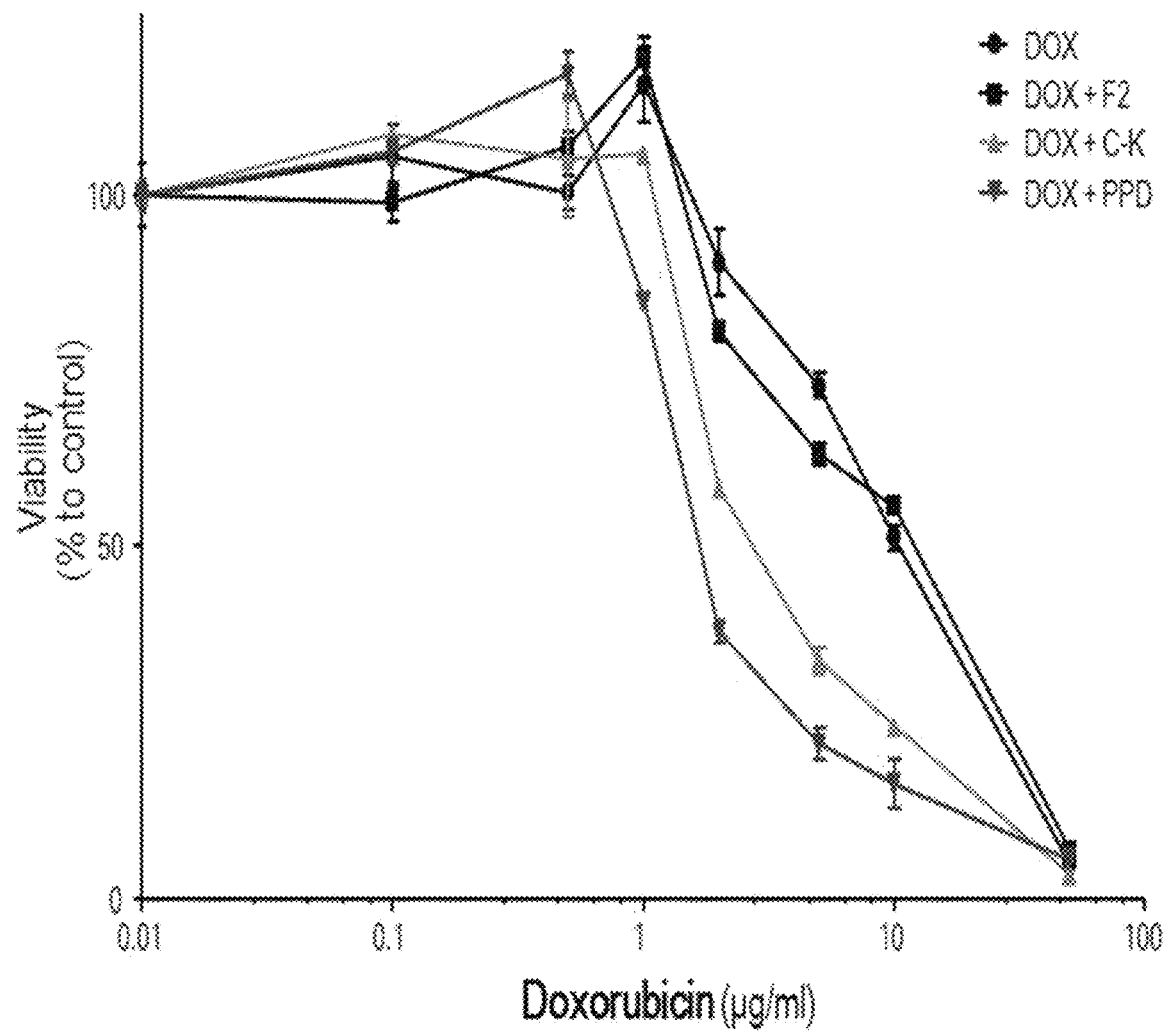
FIG. 2B shows a graph illustrating the comparison results with respect to the viability of breast cancer cells simultaneously treated with doxorubicin and C-K or PPD at various concentrations of doxorubicin, in which (●) represents negative control, (■) represents positive control, (▲) represents an experimental group treated with C-K, and (▼) represents an experimental group treated with PPD.

In this regard, to determine whether the C-K or PPD affects the treatment concentration of doxorubicin, the PPD-type ginsenoside compound (C-K or PPD) was added to the MCF-7 cells at a concentration of 10 μg/mL and cultured for 12 hours. Then, the MCF-7 cells were treated with doxorubicin at various concentrations (0 μg/mL, 0.1 μg/mL, 0.5 μg/mL, 1 μg/mL, 2 μg/mL, 5 μg/mL, 10 μg/mL, and 50 μg/mL) and cultured for 24 hours. Upon completion of the culture, the viability of the MCF-7 cells and the LC50 values calculated therefrom were compared by WST-1 assay (FIG. 2B). In particular, an experimental group not treated with ginsenoside was used as a negative control, whereas an experimental group treated with F2 (i.e., a PPD-type ginsenoside compound), which was confirmed to have no particular effect on doxorubicin, was used as a positive control.

FIG. 2B shows a graph illustrating the comparison results with respect to the viability of breast cancer cells simultaneously treated with doxorubicin and C-K or PPD at various concentrations of doxorubicin, in which (●) represents negative control, (■) represents positive control, (▲) represents an experimental group treated with C-K, and (▼) represents an experimental group treated with PPD. As shown in FIG. 2B, anticancer activity was increased when doxorubicin was treated simultaneously with C-K or PPD compared to that when doxorubicin was treated alone. In particular, comparing the LC50 values, when doxorubicin was treated alone (negative control) or when F2 and doxorubicin were treated simultaneously (positive control), the LC50 values were shown to be about 10 μg/mL, whereas when C-K and doxorubicin were treated simultaneously the LC50 values were shown to be 2 μg/mL and when PPD and doxorubicin were treated simultaneously the LC50 values were shown to be 1.5 μg/mL, thus confirming that C-K or PPD has the effect of improving the anticancer activity of doxorubicin.

Example 2-2: Effect of PPD on Expression Levels of Apoptosis-Related Proteins

Figure 3A:
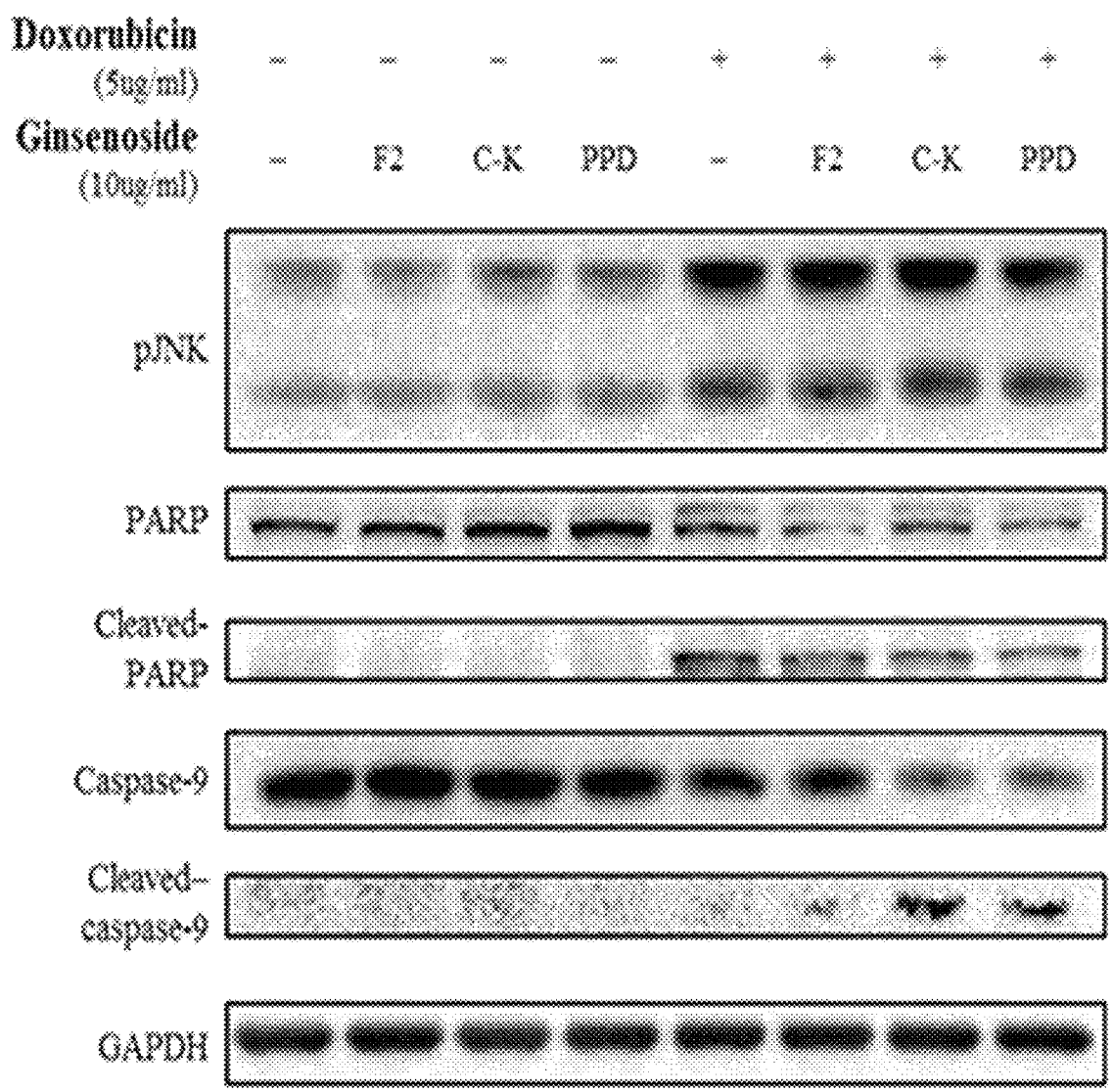
FIG. 3A shows an image of western blot analysis illustrating the comparison results with respect to the expression levels of apoptosis-related proteins in breast cancer cells simultaneously treated with C-K or PPD and doxorubicin.

MCF-7 cells were charged with a medium containing C-K or PPD (10 μg/mL) and cultured for 12 hours, and the medium was replaced with a medium containing C-K or PPD (10 μg/mL) and doxorubicin (0 μg/mL or 5 μg/mL) and cultured for 24 hours. The cells, upon completion of culture, were disrupted and western blot analyses were performed treated with respect to anti-phosphorylated JNK antibody, anti-PARP antibody, anti-cleaved-PARP antibody, and anti-caspase-9 antibody or anti-cleaved-caspase-9 antibody (FIG. 3A). In particular, an experimental group not treated with ginsenoside was used as a negative control, whereas an experimental group treated with F2 (i.e., a PPD-type ginsenoside compound), which was confirmed to have no particular effect on doxorubicin, was used as a positive control.

FIG. 3A shows an image of western blot analysis illustrating the comparison results with respect to the expression levels of apoptosis-related proteins in breast cancer cells simultaneously treated with C-K or PPD and doxorubicin. As shown in FIG. 3A, the levels of phosphorylated JNK, cleaved-PARP, and cleaved-caspase-9 were increased in all of the cells treated with doxorubicin. Additionally, the levels of phosphorylated JNK and cleaved-PARP, among the phosphorylated JNK, cleaved-PARP, and cleaved-caspase-9, were not affected by the treatment with C-K or PPD, but the level of the cleaved-caspase-9 was significantly increased, and in particular, a significant increase was confirmed when the breast cancer cells were treated with PPD.

Figure 3B:
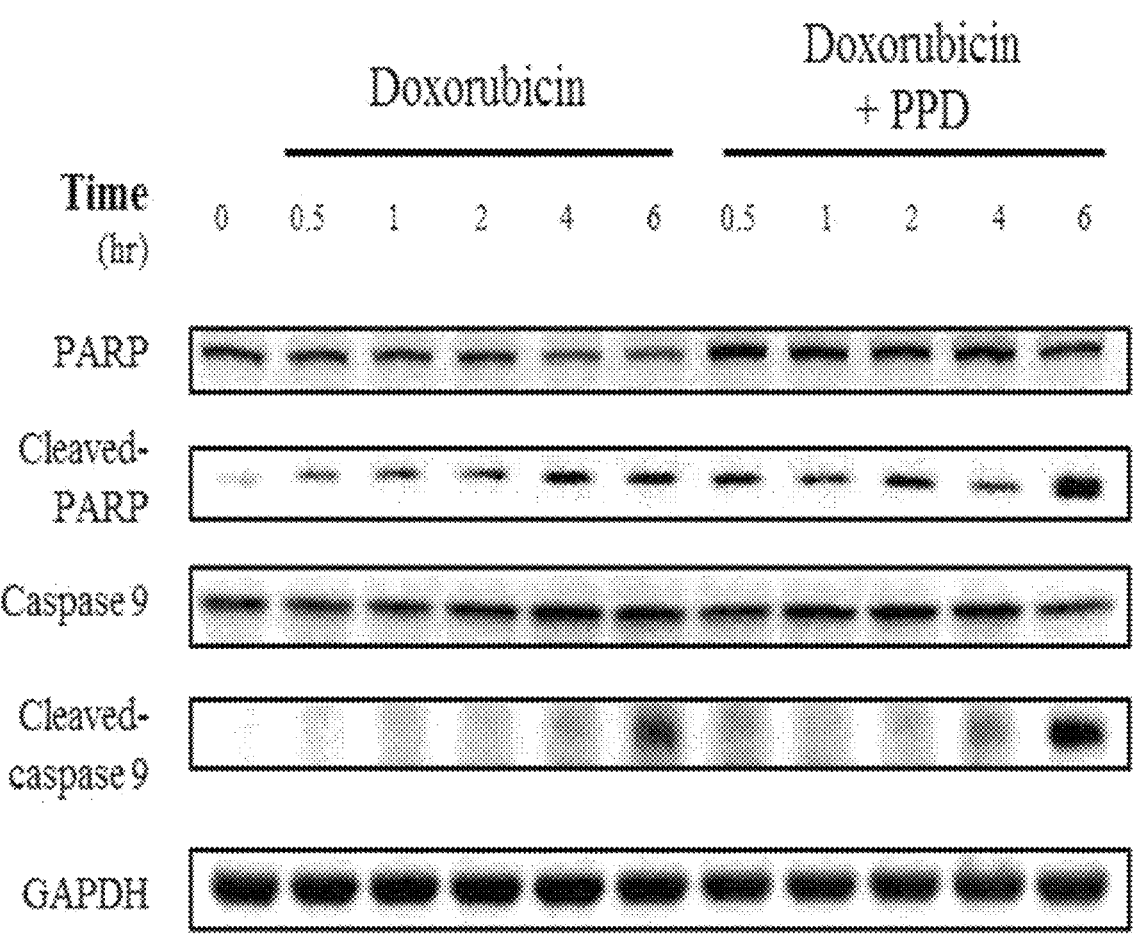
FIG. 3B shows an image of western blot analysis illustrating the comparison results with respect to the expression levels of apoptosis-related proteins in breast cancer cells simultaneously treated with PPD and doxorubicin according to treatment time.

Accordingly, MCF-7 cells were charged with a medium containing PPD (10 μg/mL) and cultured for 12 hours, and the medium was replaced with a medium containing PPD (10 μg/mL) and doxorubicin (5 μg/mL) and cultured for 0 hours, 0.5 hours, 1 hour, 2 hours, 4 hours, or 6 hours. The same western blot analysis was performed using the cultured cells (FIG. 3B). In particular, as a comparative group, cells cultured in a medium containing doxorubicin alone were used instead of the medium containing PPD and doxorubicin.

FIG. 3B shows an image of western blot analysis illustrating the comparison results with respect to the expression levels of apoptosis-related proteins in breast cancer cells simultaneously treated with PPD and doxorubicin according to treatment time. As shown in FIG. 3B, it was confirmed that cleaved-PARP and cleaved-caspase-9 were formed more rapidly in breast cancer cells treated simultaneously with PPD and doxorubicin than in breast cancer cells treated with doxorubicin alone.

From the above results, it was confirmed that PARP and caspase-9 can affect the anticancer activity of doxorubicin.

In this regard, the present inventors have attempted to confirm whether the anticancer activity of doxorubicin can be inhibited by inhibiting the activity of PARP and caspase-9.

Figure 3C:
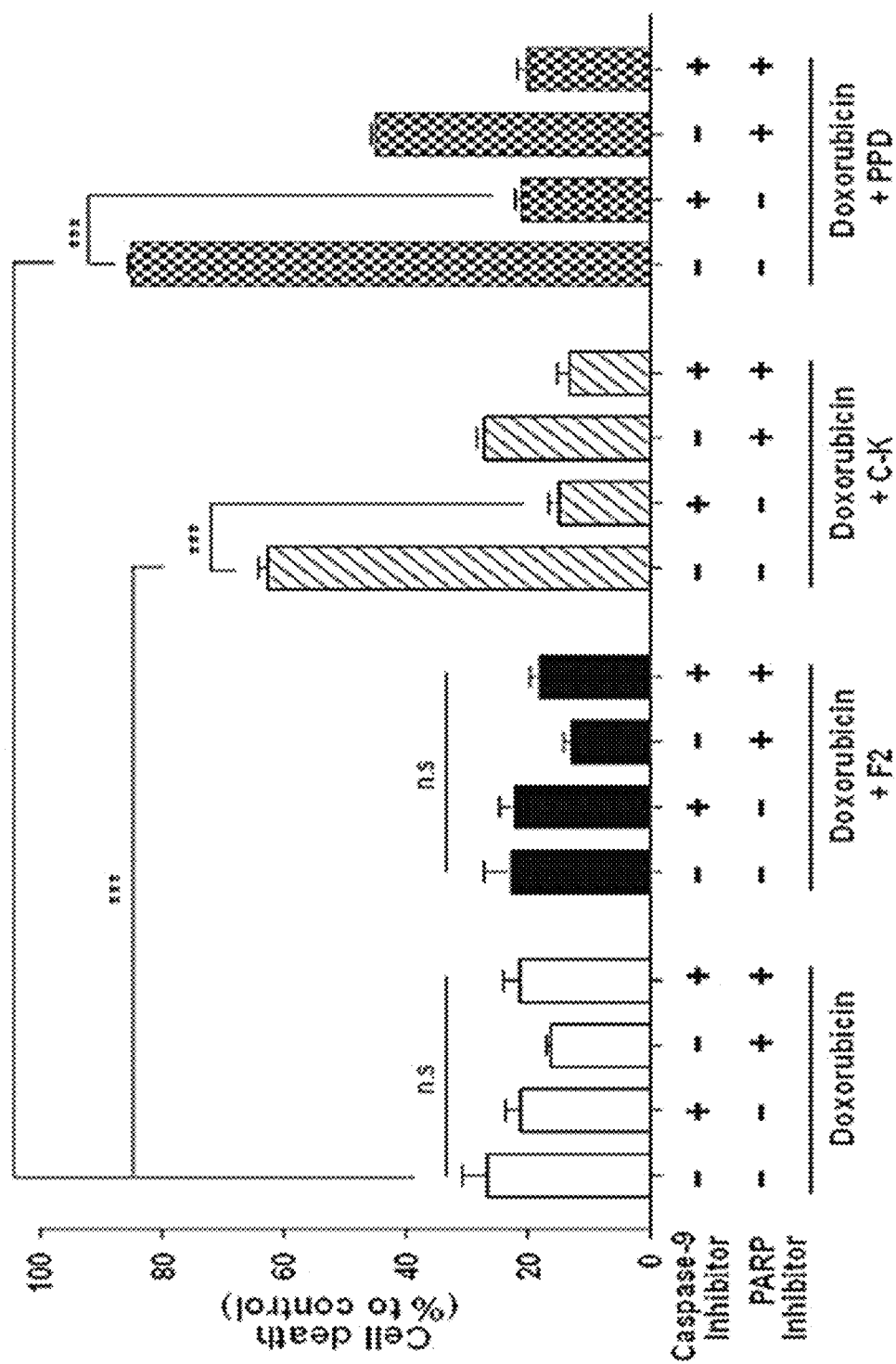
FIG. 3C shows a graph illustrating the comparison results of the effect of PARP inhibitor or caspase-9 inhibitor with respect to the anticancer activity by the simultaneous treatment with doxorubicin and C-K or PPD.

Specifically, a medium containing C-K or PPD (10 µg/mL) was added to MCF-7 cells pretreated with Z-LEHD-FMK (i.e., an inhibitor of caspase-9) or 3-AB (i.e., an inhibitor of PARP) and cultured for 12 hours. The medium was then replaced with a medium containing doxorubicin (0 µg/mL or 5 µg/mL) and cultured for 24 hours. The same western blot analysis was performed using the cultured cells (FIG. 3C). In particular, an experimental group not treated with ginsenoside was used as a negative control, whereas an experimental group treated with F2 (i.e., a PPD-type ginsenoside compound), which was confirmed to have no particular effect on doxorubicin, was used as a positive control.

FIG. 3C shows a graph illustrating the comparison results of the effect of PARP inhibitor or caspase-9 inhibitor with respect to the anticancer activity by the simultaneous treatment with doxorubicin and C-K or PPD. As shown in FIG. 3C, it was confirmed that the anticancer effect of doxorubicin was inhibited in all of the control and experimental groups treated with PARP or caspase-9 activity inhibitor. However, in the case of treatment with PARP activity inhibitor, the anticancer activity was slightly recovered when C-K or PPD and doxorubicin were treated simultaneously, which was analyzed to be due to the activity of caspase-9 located upstream of PARP.

Example 3: Effect of PPD on Mitochondria

From the results of Example 2 above, it was confirmed that C-K or PPD belonging to the PPD-type ginsenoside compounds can promote the anticancer activity of doxorubicin, an anticancer agent known to exhibit mitochondria-mediated anticancer activity. In this regard, the present inventors have made an attempt to confirm whether the C-K or PPD has an effect on mitochondria.

Example 3-1: Effect of PPD on Cytochrome-C Release Induced in Mitochondria

MCF-7 cells were charged with a medium containing C-K or PPD (10 µg/mL) and cultured for 24 hours, and the medium was replaced with a medium containing doxorubicin (5 µg/mL) and cultured for 0 hours or 4 hours. The cells, upon completion of culture, were fixed with 4% paraformaldehyde, perforated by adding 0.5% Triton X-100 solution thereto, and the cells were immunostained with anti-cytochrome-C antibody for 30 minutes. Upon completion of the staining, the cells were washed with PBS, reacted with fluorescently-labeled secondary antibody for 30 minutes, washed with PBS, and then photographed using a confocal microscope to measure the levels of fluorescence developed (FIG. 4A). In particular, an experimental group not treated with ginsenoside was used as a negative control, whereas an experimental group treated with F2 (i.e., a PPD-type ginsenoside compound), which was confirmed to have no particular effect on doxorubicin, was used as a positive control.

FIG. 4A shows immunofluorescent staining images illustrating the changes in the level of cytochrome-C released from mitochondria by simultaneous treatment with doxorubicin and C-K or PPD. As shown in FIG. 4A, it was confirmed that doxorubicin treatment increased the level of cytochrome-C release compared to no doxorubicin treatment. Even in doxorubicin treatment, the treatment with doxorubicin in combination with C-K or PPD increased the level of cytochrome-C release compared to doxorubicin treatment alone. In this regard, the present inventors have attempted to confirm whether the level of cytochrome-C release can be changed by the treatment time of doxorubicin. That is, the immunostaining was performed in the same manner as described above, except that MCF-7 cells were charged with a medium containing C-K or PPD (10 µg/mL) and cultured for 24 hours, and the medium was replaced with a medium containing doxorubicin (5 µg/mL), and the cells which were cultured for 0 hours, 0.5 hours, 1 hour, 2 hours, 4 hours, or 6 hours were used. Then, the number of cells in which cytochrome-C was released from mitochondria to cytoplasm was measured (FIG. 4B). In particular, an experimental group not treated with ginsenoside was used as a control.

FIG. 4B shows a graph illustrating the number of cells in which cytochrome-C was released from mitochondria according to the time of simultaneous treatment with doxorubicin and C-K or PPD. As shown in FIG. 4B, cytochrome-C was released in 7% of the entire cells in control treated with doxorubicin alone, whereas cytochrome-C was released in 20% of the entire cells in an experimental group treated with C-K and doxorubicin, and in an experimental group treated with PPD and doxorubicin, cytochrome-C was released in 43% of the entire cells, 6 hours after the treatment.

Accordingly, it was confirmed that C-K or PPD has an effect of promoting the release of cytochrome-c in mitochondria by doxorubicin.

Example 3-2: Effect of PPD on Damage Induction in Mitochondria

From the results of Example 3-1 above, it was confirmed that C-K or PPD can promote the release of cytochrome-c in mitochondria by doxorubicin. In this regard, the present inventors have attempted to confirm whether C-K or PPD can damage mitochondria.

That is, MCF-7 cells were charged with a medium containing C-K or PPD (10 µg/mL) and cultured for 24 hours. The cells, upon completion of culture, were fixed with 4% paraformaldehyde, perforated by adding 0.5% Triton X-100 solution thereto, and mitochondria of the cells were immunostained with anti-Tom-20 antibody. Upon completion of staining, the cells were washed with PBS and then photographed using a confocal microscope to measure the levels of fluorescence developed (FIG. 5A). In particular, an experimental group not treated with ginsenoside was used as a negative control, whereas an experimental group treated with F2 (i.e., a PPD-type ginsenoside compound), which was confirmed to have no particular effect on doxorubicin, was used as a positive control.

FIG. 5A shows immunofluorescent staining images of mitochondria contained in MCF-7 cells treated with C-K or PPD. As shown in FIG. 5A, the mitochondria in the positive control showed no noticeable change compared to those in the negative control, however, damage was observed in the mitochondria contained in the MCF-7 cells treated with C-K or PPD.

Accordingly, western blot analysis was performed with respect to each of the cultured cells and the expression levels of the proteins (Drp1, Fis1, and OPA-3) involved in mitochondrial fission and those of the proteins (Mfn1, Mfn2, and OPA1) involved in mitochondrial fusion were compared (FIG. 5B).

FIG. 5B shows an image of western blot analysis illustrating the expression levels of the proteins involved in mitochondrial fission expressed in MCF-7 cells treated with C-K or PPD (Drp1, Fis1, and OPA-3) and the proteins involved in mitochondrial fusion (Mfn1, Mfn2, and OPA1).

As shown in FIG. 5B, the MCF-7 cells treated with C-K or PPD showed an increase in the expression level of OPA-3, a protein involved in mitochondrial fission, while the expression level of Mfn2, a protein involved in mitochondria fusion, is decreased Summarizing the results of Examples 3-1 and 3-2 above, it was confirmed that C-K or PPD can induce mitochondrial damage. Therefore, when C-K or PPD is co-treated with doxorubicin, C-K or PPD can increase the releasing process of cytochrome-C being released from mitochondria by doxorubicin treatment thereby increasing the anticancer activity of doxorubicin.

Example 4: Analysis of Correlation Between Mitochondrial Fission and Anticancer Activity of Doxorubicin From the results of Example 3-2 above, it was confirmed that C-K or PPD can induce mitochondrial damage. Therefore, the present inventors have attempted to analyze the correlation between mitochondrial fission and anticancer activity of doxorubicin by inducing mitochondrial fission via inhibition of the expression of the proteins (Mfn1 or Mfn2), which are involved in mitochondrial fusion, followed by doxorubicin treatment.

Specifically, siRNAs targeting Mfn1 and Mfn2 were synthesized, and random siRNAs were synthesized as a negative control.

```
Control:
                               (SEQ ID NO: 1)
5'-CCUACGCCAAUUUCGU-3'-dTdT Mfn1:
                               (SEQ ID NO: 2)
5'-GUGUAGAUUCUGGUAAUGA-3'-dTdT Mfn2:
                               (SEQ ID NO: 3)
5'-CGAUGCAACUCUAUCGUCA-3'-dTdT
```

Each of the synthesized siRNAs was introduced into MCF-7 cells and cultured for 12 hours. The cells were cultured further for 48 hours in a normal medium containing no siRNA and the expression levels of the proteins (Mfn1 and Mfn2) involved in mitochondrial fusion expressed in these cells were confirmed by western blot analysis (FIG. 6A).

Figure 6A:
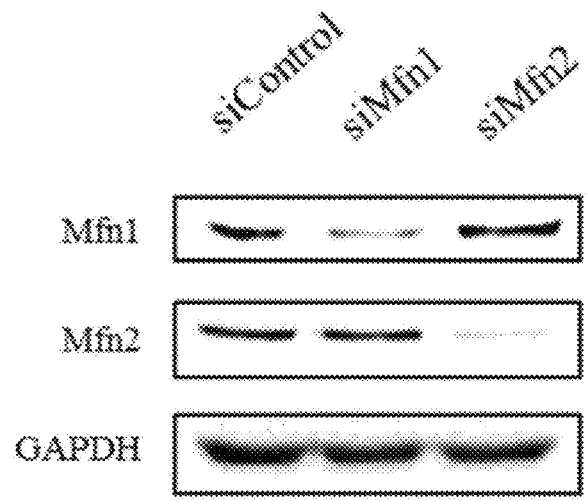
FIG. 6A shows an image of western blot analysis confirming the results of inhibiting the expression of the proteins (Mfn1 and Mfn2), which are involved in mitochondrial fusion, by siRNA that inhibits the expression of the proteins.
Figure 6B:
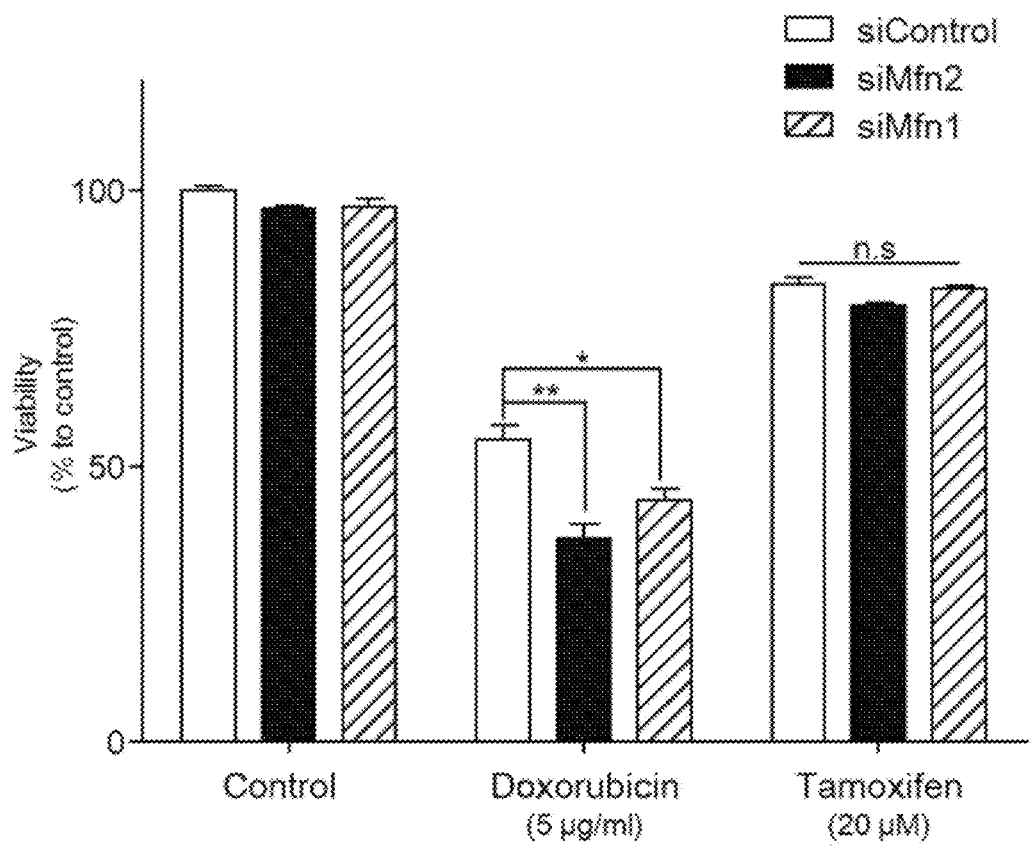
FIG. 6B shows a graph illustrating the comparison results with respect to anticancer activity of doxorubicin and tamoxifen in cells where the mitochondrial fission was induced.

FIG. 6A shows an image of western blot analysis confirming the results of inhibiting the expression of the proteins (Mfn1 and Mfn2), which are involved in mitochondrial fusion, by siRNA that inhibits the expression of the proteins. As shown in FIG. 6A, it was confirmed that the expression of the proteins (Mfn1 and Mfn2) involved in mitochondrial fusion was inhibited by the introduction of the siRNA.

Meanwhile, each of the synthesized siRNAs was introduced into MCF-7 cells and cultured for 12 hours. The cells were cultured further for 48 hours in a normal medium containing no siRNA, treated with 5 µM doxorubicin or 20 µM tamoxifen, and cultured for 24 hours. Upon completion of culture, the viability of the MCF-7 cells was compared by WST-1 assay (FIG. 6B). In particular, an experimental group not treated with doxorubicin or tamoxifen was used as a control.

FIG. 6B shows a graph illustrating the comparison results with respect to anticancer activity of doxorubicin and tamoxifen in cells where the mitochondrial fission was induced. As shown in FIG. 6B, the cells not treated with doxorubicin or tamoxifen did not show a decrease of viability even after the mitochondrial fission was induced, whereas the cells treated with doxorubicin or tamoxifen showed anticancer activity, and in particular, a significantly high level of anticancer activity was shown when doxorubicin was treated rather than tamoxifen. Additionally, it was confirmed that, in the case where mitochondrial fission was induced, anticancer activity of doxorubicin was further increased when the expression of Mfn2 was inhibited compared to when the expression of Mfn1 was inhibited. However, when tamoxifen was treated, it was confirmed that there was no difference in anticancer activity according to the treatment of each of the siRNAs.

Figure 7:
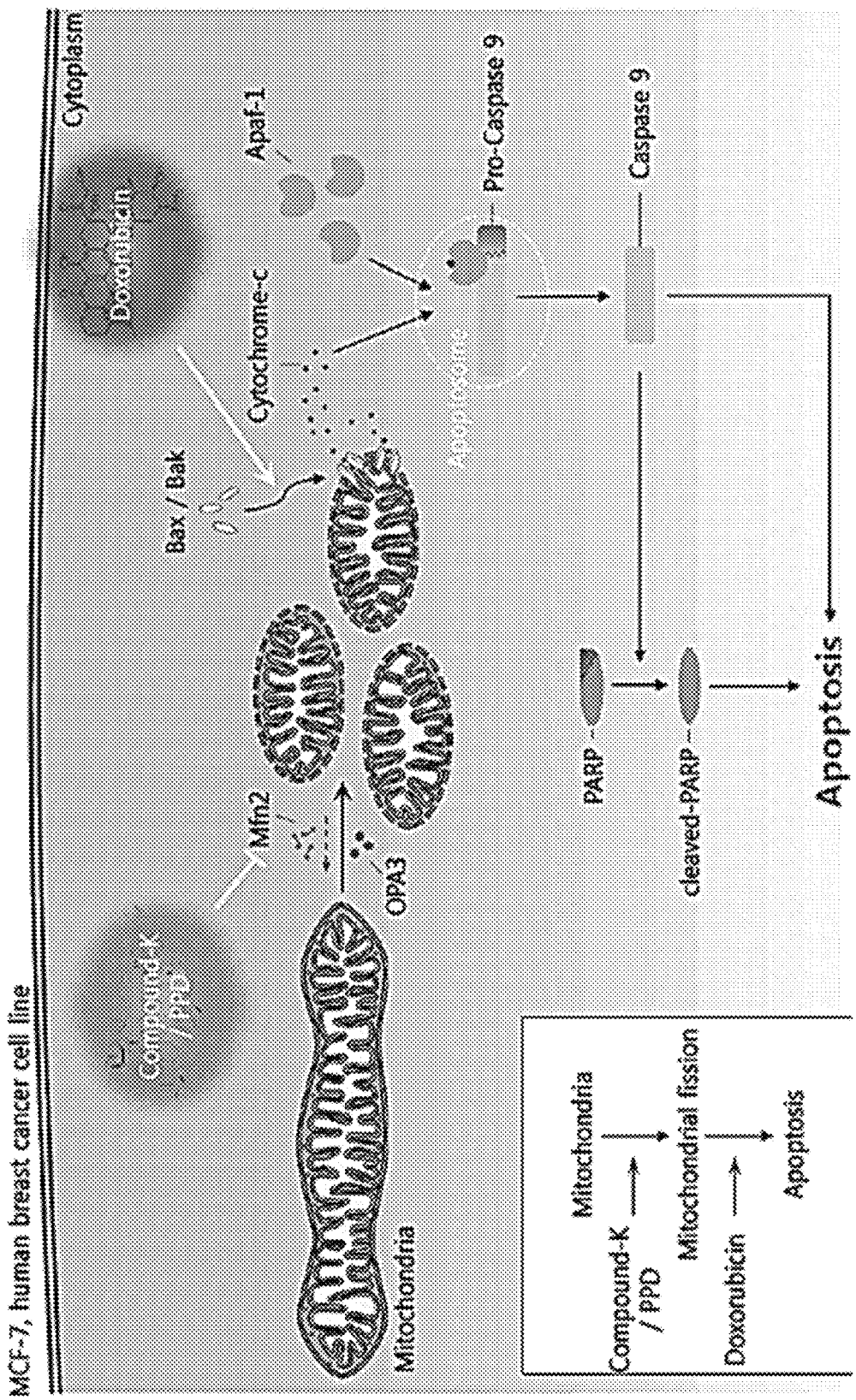
FIG. 7 is a schematic diagram illustrating the mechanism with regard to anticancer activity of the anticancer adjuvant and the anticancer agent having mitochondria-mediated anticancer activity provided by the present invention.

Summarizing the results of Examples 1 to 4, as shown in FIG. 7, C-K or PPD belonging to PPD-type ginsenoside compounds inhibits the expression of Mfn2, which belongs to the mitochondria fusion proteins, thus promoting mitochondrial fission and resulting in damage to mitochondria. Treatment of cancer cells in this state with an anticancer agent (doxorubicin), which exhibits mitochondria-mediated anticancer activity, further damages the outer membrane of the damaged mitochondria, resulting in a further increase in the release of cytochrome-C from the mitochondria to the cytoplasm, and the cytochrome-C released as such induces apoptosis through apoptosomes, thereby causing the death of cancer cells.

Accordingly, it was confirmed that when the combination treatment with C-K or PPD and an anticancer agent exhibiting mitochondria-mediated anticancer activity can reduce the dose of the anticancer agent and thereby more safe anticancer treatment can be performed.

The invention claimed is:

1. A method for enhancing or increasing the effectiveness of an anticancer agent having a mitochondria-mediated anticancer activity for treating breast cancer, wherein the method comprises:
   administering to a subject having breast cancer an anticancer adjuvant comprising compound K and the anticancer agent,
   wherein the anticancer adjuvant is administered at a concentration that is not cytotoxic to the cancer cells,
   wherein administration of the anticancer adjuvant with the anticancer agent allows for use of the anticancer agent at a lower effective standard dose.

2. The method of claim 1, wherein compound-K is a compound having the structure of the following Formula 2:

[Formula 2]

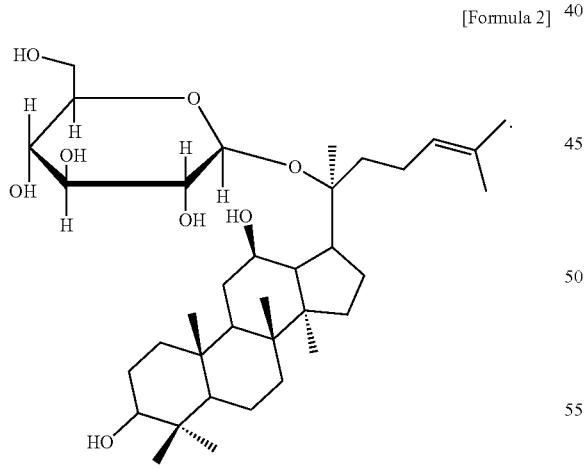

3. The method of claim 1, wherein the anticancer adjuvant is used at a concentration of 0.1 µg/mL to 10 µg/mL.

4. A method for treating breast cancer in a subject in need thereof, comprising administering to the subject a pharmaceutical composition comprising doxorubicin, and compound-K as active ingredients,
   wherein compound-K is used as an anticancer adjuvant to increase or enhance the effectiveness of doxorubicin in treating breast cancer, and
   wherein administration of the pharmaceutical composition comprising doxorubicin and compound-K allows for treatment of the breast cancer with doxorubicin at a lower effective standard dose.

5. The method of claim 4, wherein compound-K is a compound having the structure of the following Formula 2:

[Formula 2]

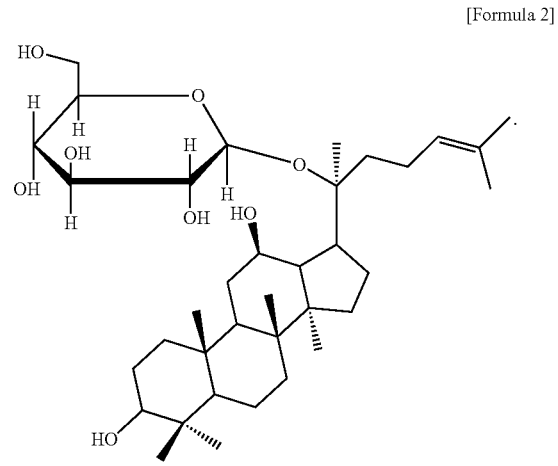

* * * * *